(12) United States Patent
Tanghoej et al.

(10) Patent No.: US 6,635,036 B1
(45) Date of Patent: Oct. 21, 2003

(54) VALVE SYSTEM FOR A COLLECTION BAG

(75) Inventors: Allan Tanghoej, Kokkedal (DK); Thomas Friis Joergensen, Holbaek (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 09/622,929

(22) PCT Filed: Jan. 29, 1999

(86) PCT No.: PCT/DK99/00046

§ 371 (c)(1),
(2), (4) Date: Sep. 8, 2000

(87) PCT Pub. No.: WO99/45866

PCT Pub. Date: Sep. 16, 1999

(30) Foreign Application Priority Data

Mar. 9, 1998 (DK) .............................................. 0319/98

(51) Int. Cl.[7] .............................................. A61M 1/00
(52) U.S. Cl. ...................................... 604/323; 604/335
(58) Field of Search ................................. 604/317, 322, 604/323, 325, 326, 327, 346, 349, 328–331, 335; 251/351, 95, 96, 252, 251, 352, 353, 349; 137/615, 616.3, 616.5, 616.7

(56) References Cited

U.S. PATENT DOCUMENTS

| | | | | |
|---|---|---|---|---|
| 4,408,631 A | * | 10/1983 | Uhlig et al. ................. | 137/380 |
| 4,512,770 A | * | 4/1985 | Cianci et al. ................ | 604/323 |
| 4,579,126 A | * | 4/1986 | Cianci ........................ | 128/767 |
| 4,603,837 A | | 8/1986 | Steer .......................... | 251/352 |
| 4,640,494 A | * | 2/1987 | Steer .......................... | 251/354 |
| 4,844,415 A | * | 7/1989 | Nielsen et al. .............. | 251/325 |
| 4,909,478 A | * | 3/1990 | Steer .......................... | 251/352 |
| 5,429,624 A | * | 7/1995 | Coelho, Jr. .................. | 604/323 |
| 6,129,684 A | * | 10/2000 | Sippel et al. ................ | 600/575 |

FOREIGN PATENT DOCUMENTS

| | | |
|---|---|---|
| GB | 2 118 685 | 11/1983 |
| GB | 2 285 496 | 7/1995 |
| WO | 93/17642 | 9/1993 |

* cited by examiner

*Primary Examiner*—Weilun Lo
*Assistant Examiner*—Michele Kidwell
(74) *Attorney, Agent, or Firm*—Jacobson Holman PLLC (57) ABSTRACT

The invention concerns an outlet valve system for a collection bag for urine from urine-incontinent or urostomy operated humans. Collection bags for urine are well known and typically consist of plastic sheets which are joined by welding along their peripheries to form a cavity between the sheets in which the urine is collected. When out of bed the user normally carry the bag by the lower part of the leg and in order to discharge urine from the bag, the bag is supplied with an outlet valve system at its lowermost part. The valve system comprises a base member which is secured to the collection bag and a movable member which is sealingly fixed to the base member; the base member has an open conduct leading into the cavity of the collection bag and conducting liquid to the movable member. The movable member has a discharge tube which is rotatably displaceable with respect to the base member and which is rotated out of the plane defined by the outer surface of the collection bag. The movable member has at least one open position and at least one secured closed position where the discharge tube is pointing upwards. In the open position is the discharge tube rotated to a position situated between more than 90° and less than 180° from upright vertical and here the discharge tube is secured.

18 Claims, 10 Drawing Sheets

VALVE SYSTEM FOR A COLLECTION BAG

FIELD OF THE INVENTION

The invention concerns an outlet valve system for a collection bag for urine from urine-incontinent or urostomy operated humans. The valve system comprises a base member which is secured to the collection bag and a movable member which is sealingly fitted to the base member; the base member has an open conduit leading into the cavity of the collection bag and conducting liquid to the movable member. The movable member has a discharge tube which is rotatably displaceable with respect to the base member and which is rotated out of the plane defined by the outer surface of the collection bag. The movable member has at least one open position and at least one secured closed position where the discharge tube is pointing upwards.

Collection bags for urine are well known and typically consists of plastic sheets which are joined by welding along their peripheries to form a cavity between the sheets in which the urine is collected. When out of bed the user normally carry the bag by the lower part of the leg and in order to discharge urine from the bag, the bag is supplied with an outlet valve system at its lowermost part.

When the bag is full it is possible for the user to empty the bag and reuse it. Discharge of urine from the valve system takes place through a tube or hose member having a discharge opening which forms part of the valve system. At least a few drops of urine will always be left in the discharge tube or hose member, and in order to prevent malodours from such drops it is necessary to prevent these drops from getting in contact with the users clothes or body. To prevent this the drops can either be removed or the opening of the discharge hose can be plugged or placed in an upright position. An advantage of placing the discharge tube in an upright position when closed is that the bag including the valve system is shorter and nothing sticks out of the trouser leg.

BACKGROUND OF THE INVENTION

In WO 93/17642 is a valve system for a urine collection bag demonstrated. This valve system has a base member (10) being secured to the bag and a movable means (20). The movable means is formed by a discharge tube member having an inlet section (21), a tube section (22) and a discharge opening (23). The inlet section (21) is sealingly engaged around a cylindrical portion (12) of the base member and the movable means are able to rotate around this cylindrical portion (12). The cylindrical portion (12) of the base member is hollow and supplied with a hole (14) through which liquid can pass into the movable means (20). The movable means can rotate between two positions (FIGS. 4 and 5); in the first position (FIG. 5) the movable means has been rotated to a position in which the tube section (22) is arranged concentric opposite the hole (14) in the cylindrical portion (12) of the base part which allows urine to pass from the bag out through the valve system; in the second position (FIG. 4) the movable means has been rotated to a position in which the walls of the inlet section (21) totally covers the hole (14) and no urine can pass through the valve system.

When this valve is open and urine flowing out of the discharge opening the user need to direct the flow away from the vertical plane in order to avoid the flow of urine getting in contact with the footwear. This operation of reaching to the feet can be very difficult for users who are placed in a wheel chair such as paraplegics or for other users with low motility.

The valve in this document also has to be placed on a relatively flat part of the bag in order to be able to rotate the tube section easily and this will increase the length of the construction of the bag and valve system.

Another valve system is known from British Patent Application no. 2 285 496. The valve described in this document is opened and closed by relative rotation of its inlet and outlet pipes (12,18) about an axis perpendicular to their longitudinal axes. The inlet and outlet pipes (12,18) project from housing parts (14,16). One housing part has a barrel fitting inside the other housing part. The valve is open when the inlet pipe (12) is upright and the outlet pipe (18) points downward as the housing parts each have an aperture that are in alignment when the pipes are aligned this way (FIG. 1). When the pipes both face the same direction the valve is closed. The outlet pipe (18) according to this invention can be rotated at least 180° relative to the inlet pipe (12).

Also with this valve care has to be taken in guiding the discharge from the outlet pipe away from the users leg and shoe when the bag is emptied.

BRIEF DESCRIPTION OF THE INVENTION

In the valve system according to this invention the discharge tube is rotated to an open position situated between more than 90° and less than 180° from upright vertical and here the discharge tube is secured.

With the discharge tube in this open position it is not necessary for the user to hold the discharge tube while the outflow is directed away from the users leg. Also the bag and valve system will be as short as possible with the discharge tube in the upward closed position.

The construction of this valve system is simple and the system is easy to use even for elderly or disabled users with limited motility and strength as the movements of the discharge tube is firmly guided and leaves the user little possibility to accidentally leave or push the tube into the open position.

In a preferred embodiment of the valve system the discharge tube has at least three secured positions. The first is the upward closed position, the second is a downward closed position and the third is a downward open position. This embodiment increases the users control of when to drain urine from the bag and when to keep it closed.

BRIEF DESCRIPTION OF THE DRAWINGS

The invention will be described in more details below with reference to the drawings, in which.

DETAILED DESCRIPTION OF THE INVENTION

Figure 1A:
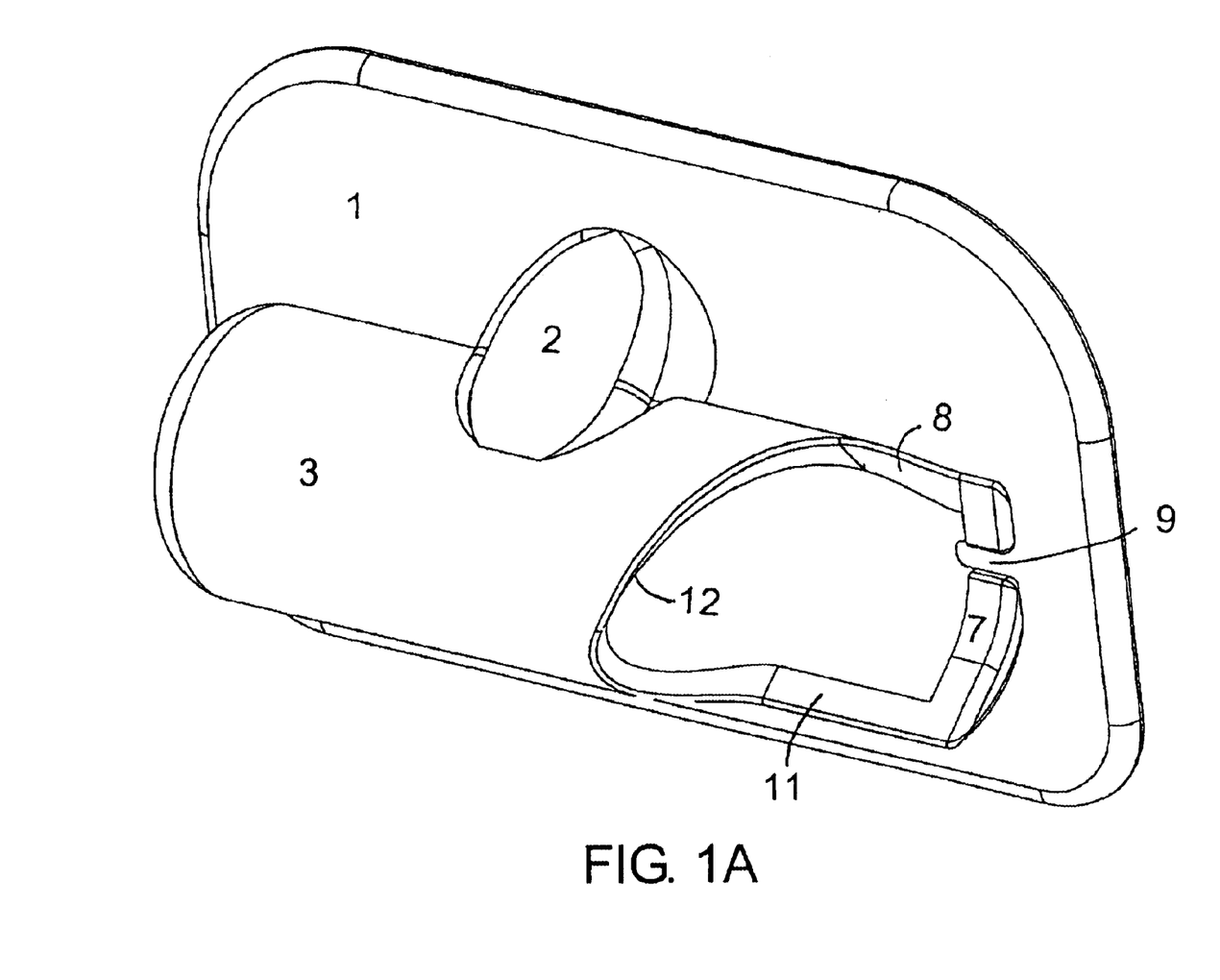
FIGS. 1a and 1b shows two examples of base members according to the invention.
Figure 1B:
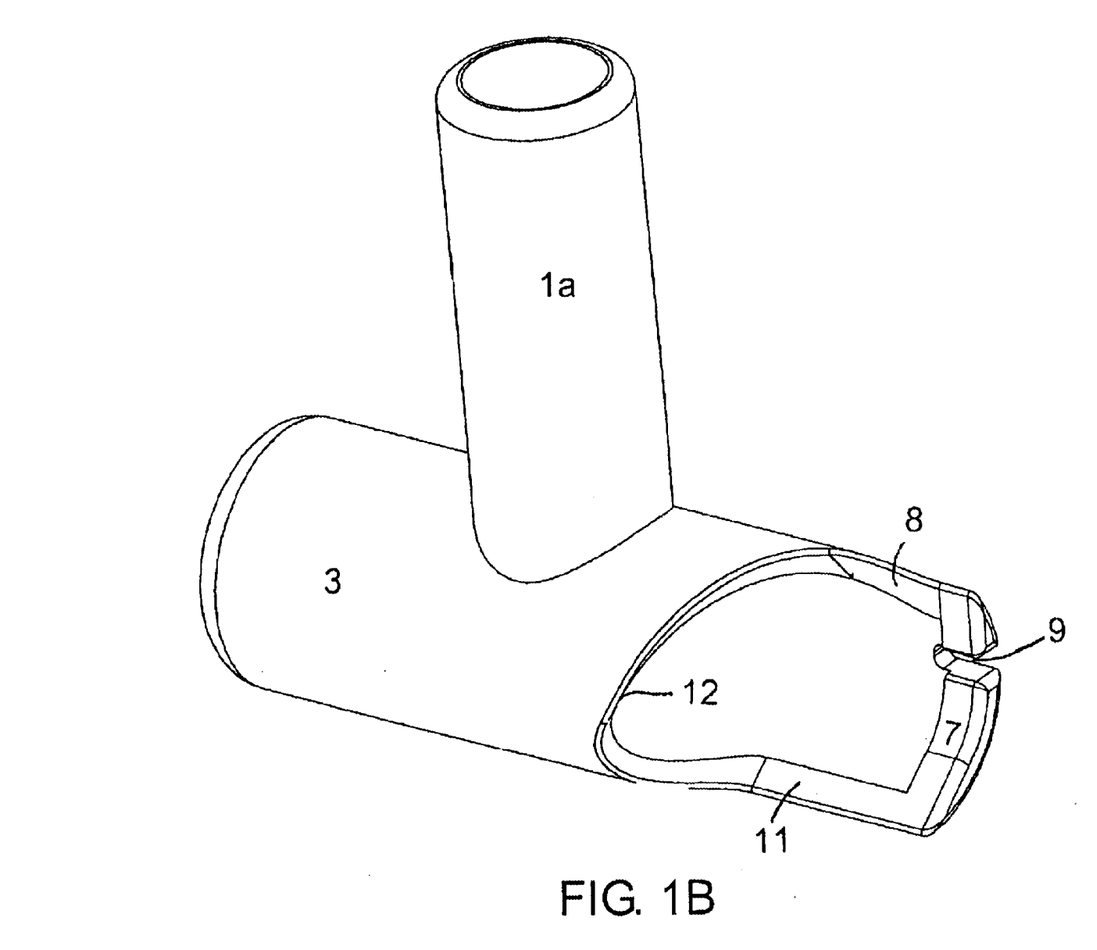

The base member in FIG. 1A is a preferred embodiment of the invention and consists of a plate 1, a conduit 2 and a container 3. Fluid from the bag passes freely through a hole in the plate 1 into the conduit 2. Whether the fluids are stopped or flow through the conduit 2 into the container 3 of the base member depends on the position of the movable member. The base member does not need to be fastened to the bag via a plate 1; it might be fastened to the bag via an inlet tube 1a as shown in FIG. 1B where the inlet tube replaces the plate 1 and the conduit 2. No matter what the form of the base member is, the base member can be fastened to the bag by welding.

Figure 2A:
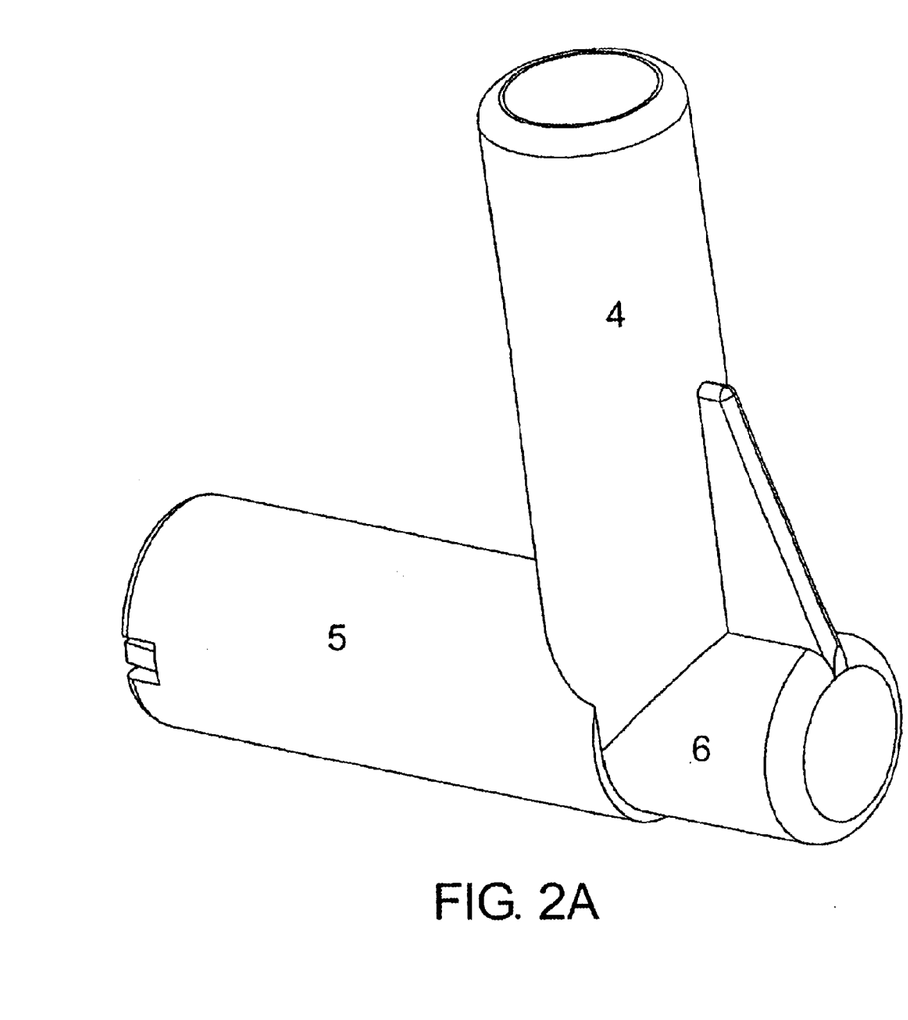
FIGS. 2a and 2b shows an example of a movable member according to the invention.
Figure 2B:
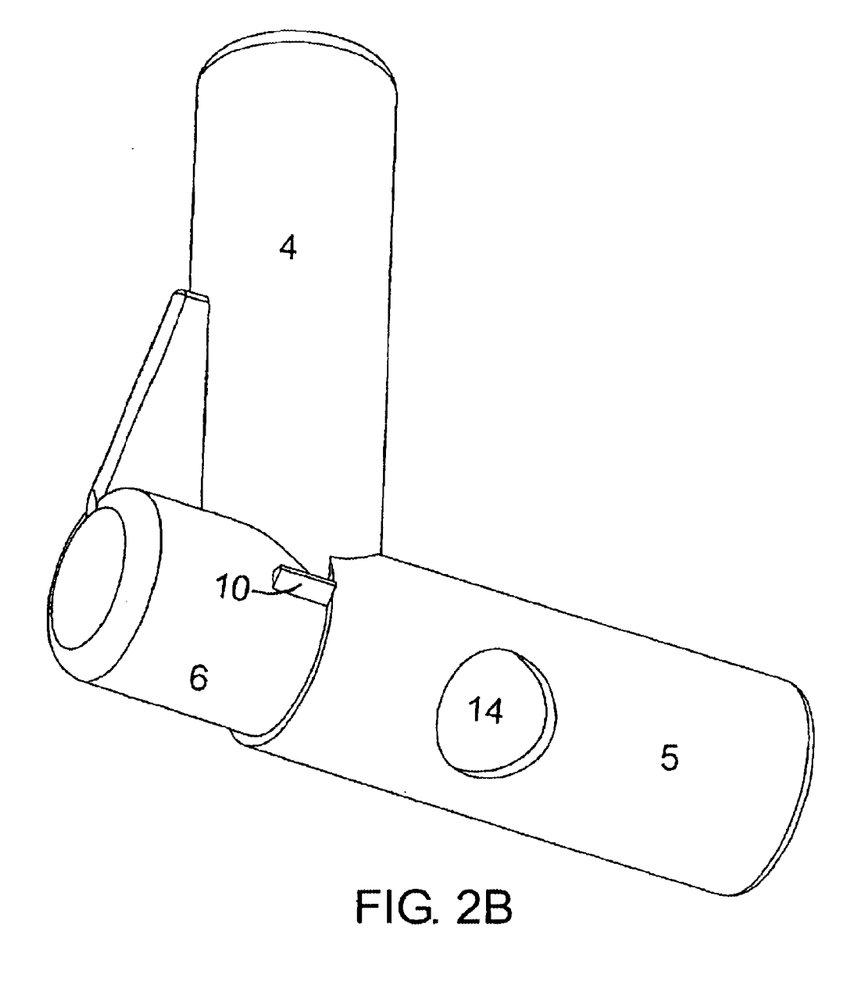

In FIGS. 2A and 2B is shown a preferred embodiment of the movable member. In FIG. 2A the movable member is seen from the front side and in FIG. 2B from the back side (the side turned towards the user). The movable member comprises a discharge tube 4, an internal part 5 and an external part 6. The internal part 5 is sealingly and rotatably inserted into the container 3 of the base member. The internal part 5 is at least partly hollow which means that fluids, when the valve is open, can pass from a hole 14 in the wall of the internal part 5 which corresponds with the conduit 2 of the base member, through the internal part 5 and out of the discharge tube 4. In this preferred embodiment of the movable member, the outside of the internal part 5 has a larger diameter than the outside of the external part 6. This feature secures a limited axial movement of the movable part along the axis of rotation as the base member is provided with an inward turned bead 7 which the internal part 5 with the increased diameter cannot pass. If it is chosen to make the movable part without the external part 6, the inward turned bead 7 can be replaced with an end wall which totally or partly covers the end of the container 3.

The forming of a cut out of the container 3 limited by two straight edges, a lower 11 and an upper 8, and a curved edge 12, combined with guiding means placed on the surfaces between the movable member and the base member, determines the tracks along which the movable member moves. Thus in the preferred embodiment of the base member which is showed in the figures the valve opens in two step and closes in one step.

Rotation of the movable member to the upward and closed position is stopped when the upper side of the discharge tube meets the upper edge 8 of cut out of the container 3 and this position of the movable member can be secured by a groove 9 in the inward turned bead 7. This groove 9 corresponds to a projection 10 on the external part 6 of the movable member. When the valve is to be opened, the projection 10 is forced out of the groove 9 and then the movable member is rotated to a downward position. The rotation is stopped when the lower side of the discharge tube 4 touches the lower edge 11 of the cut out of the container 3. To open the valve it is now necessary to push the movable member axially to the left along the axis of rotation until the left side of the discharge tube 4 touches the curved edge 12. When the movable member is in this position, the hole in the conduit 2 corresponds with the hole 14 in the movable member and the liquid flows out of the collection bag. When the user wants to close the valve it is only necessary to push the movable member upwards, as the inclined curved edge 12 assures that the movable member is both displaced axially and upwards.

In order to open the valve in one step and close in one step the curved edge 12 would have to be approximately vertical.

Figure 3:
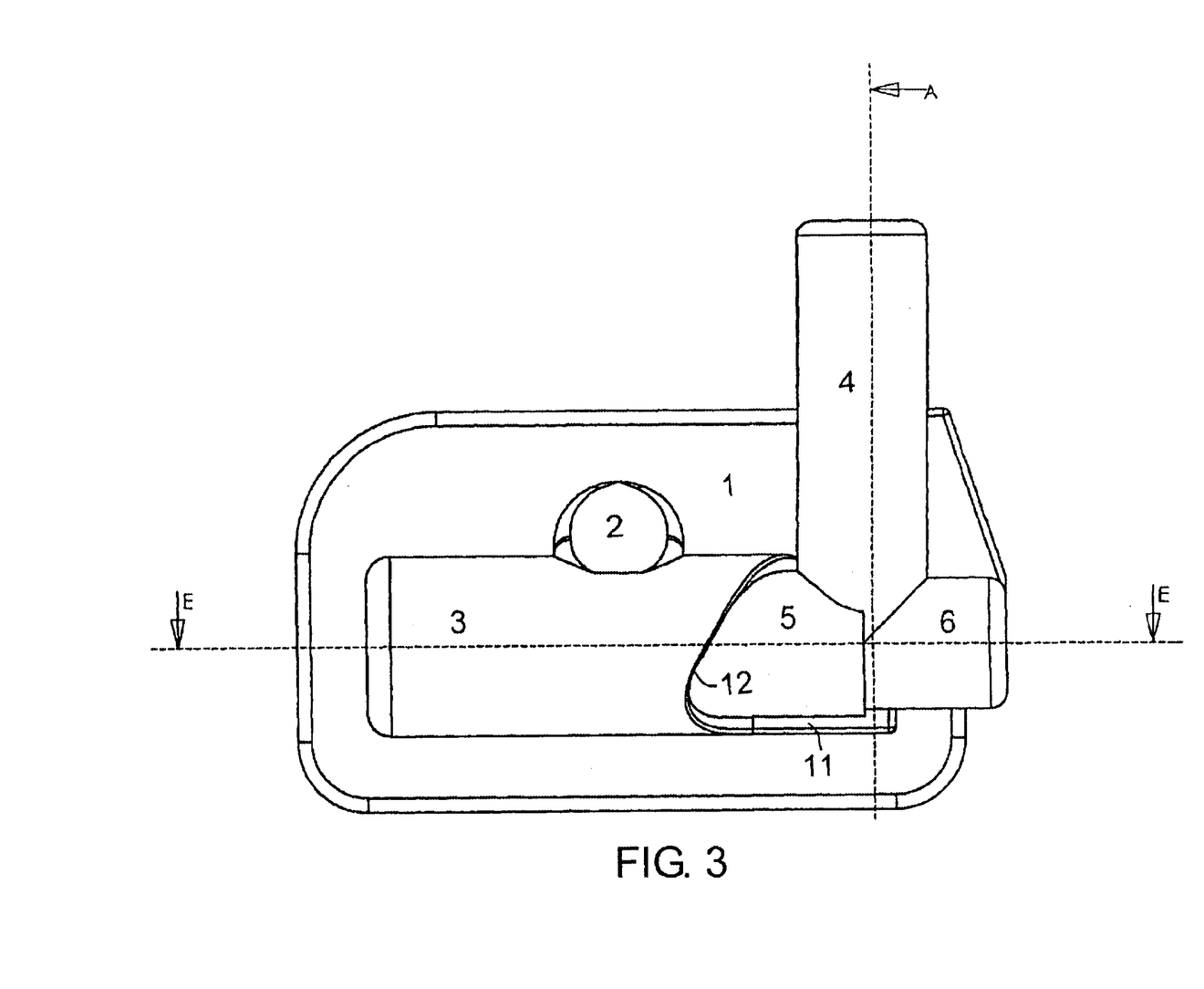
FIG. 3 shows the base member and the movable member combined as a valve system with the discharge tube in an upward closed position.

FIG. 3 shows the base member and the movable member combined into a valve system and the system is showed when being in an upward closed position.

Figure 4:
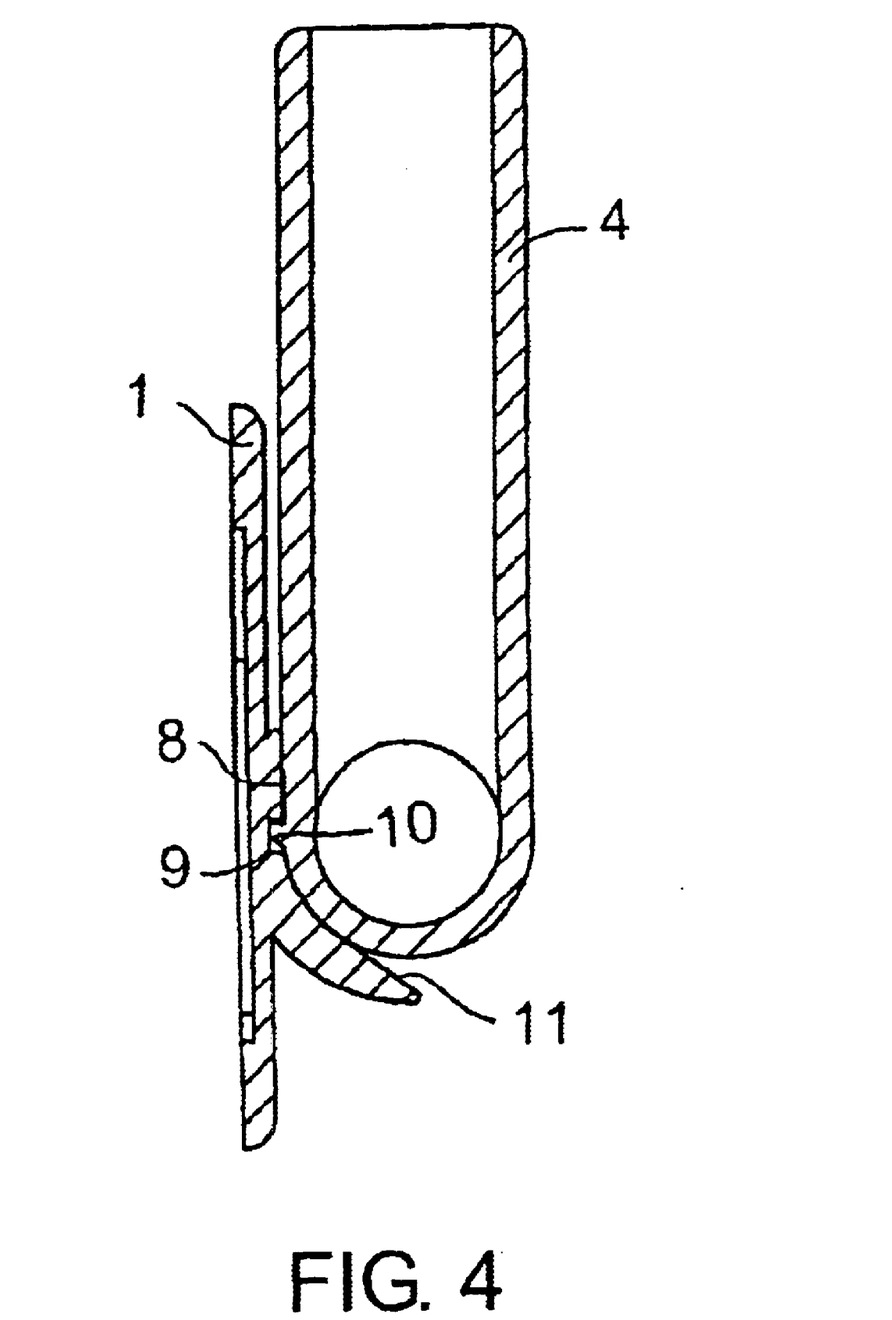
FIG. 4 shows a cut A—A through the combined valve system with the discharge tube in the upward closed position.

FIG. 4 shows a cut A—A through FIG. 3. Here it is possible to see the groove 9 of the base member and the projection 10 of the movable member which secures the movable member in the upward closed position.

Figure 5:
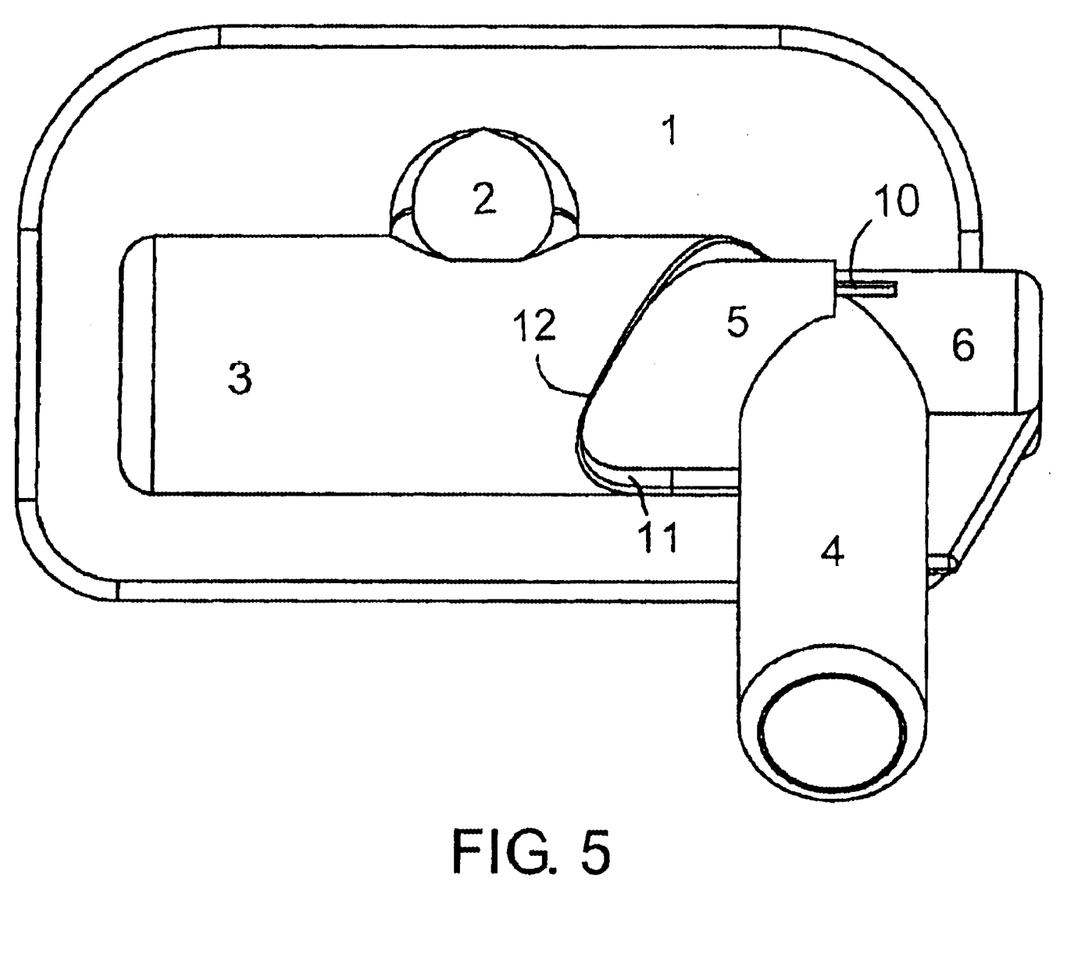
FIG. 5 shows the base member and the movable member combined as a valve system with the discharge tube in a downward closed position.

FIG. 5 shows the combined valve system in a downward closed position. To get the movable member to this position the projection 10 has to be forced out of the groove 9 and the discharge tube 4 afterwards has to be rotated to the downward position.

Figure 6:
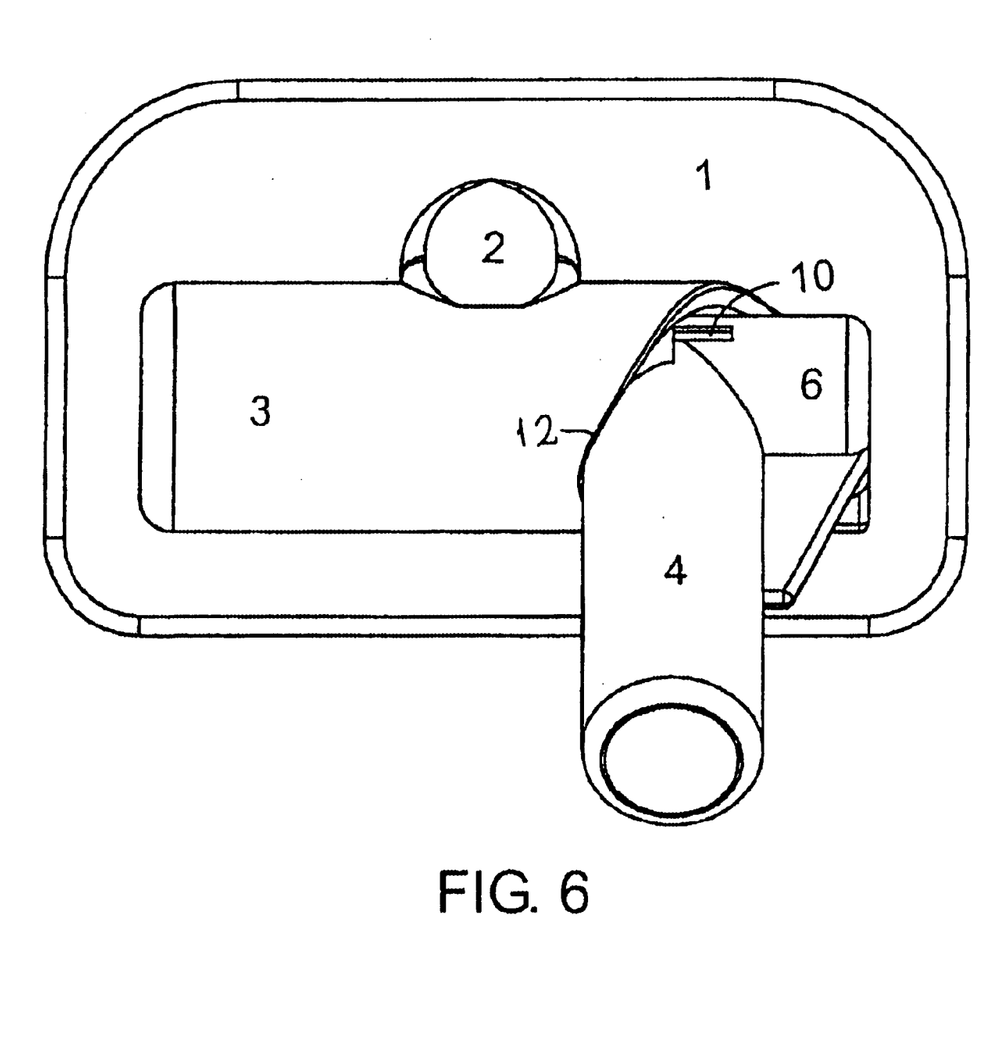
FIG. 6 shows the base member and the movable member combined as a valve system with the discharge tube in a downward open position.

FIG. 6 shows the valve system in a downward open position where liquid flows in through the conduit 2, through the hole 14 into the hollow internal part 5 and passes out through the discharge tube 4.

Figure 7:
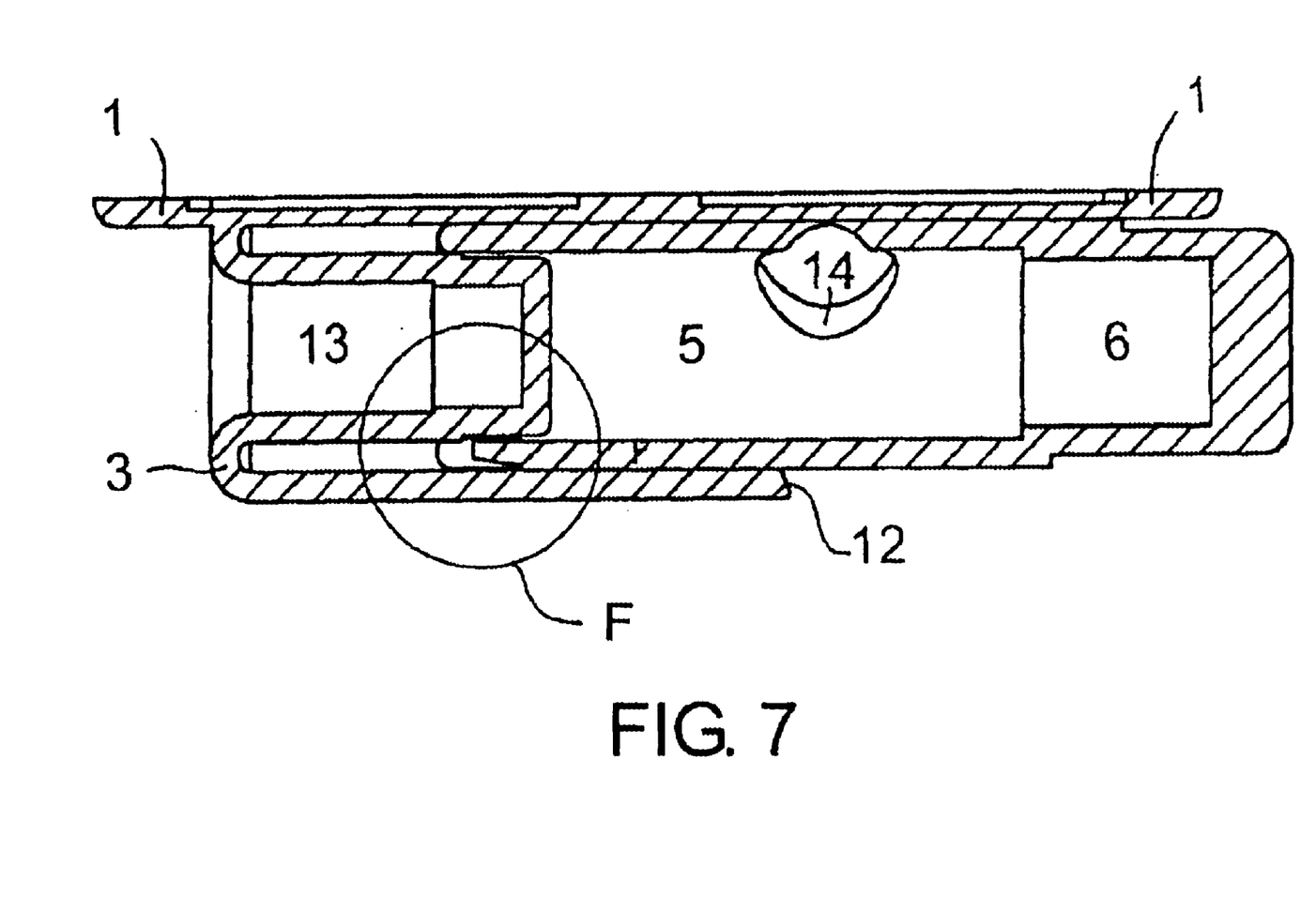
FIG. 7 shows a cut E—E seen from above through the valve system of FIG. 3.

FIG. 7 shows a cut E—E through the valve system of FIG. 3. In this embodiment of the valve system the container 3 has been made with a bowl shaped cavity 13 in the one end. The movable member also has a bowl shaped cavity at the internal part 5 and this cavity fits very tightly around the cavity of the base member. This bowl shape of the two members prevents an accumulation of urine in the end of the container 3.

Figure 8:
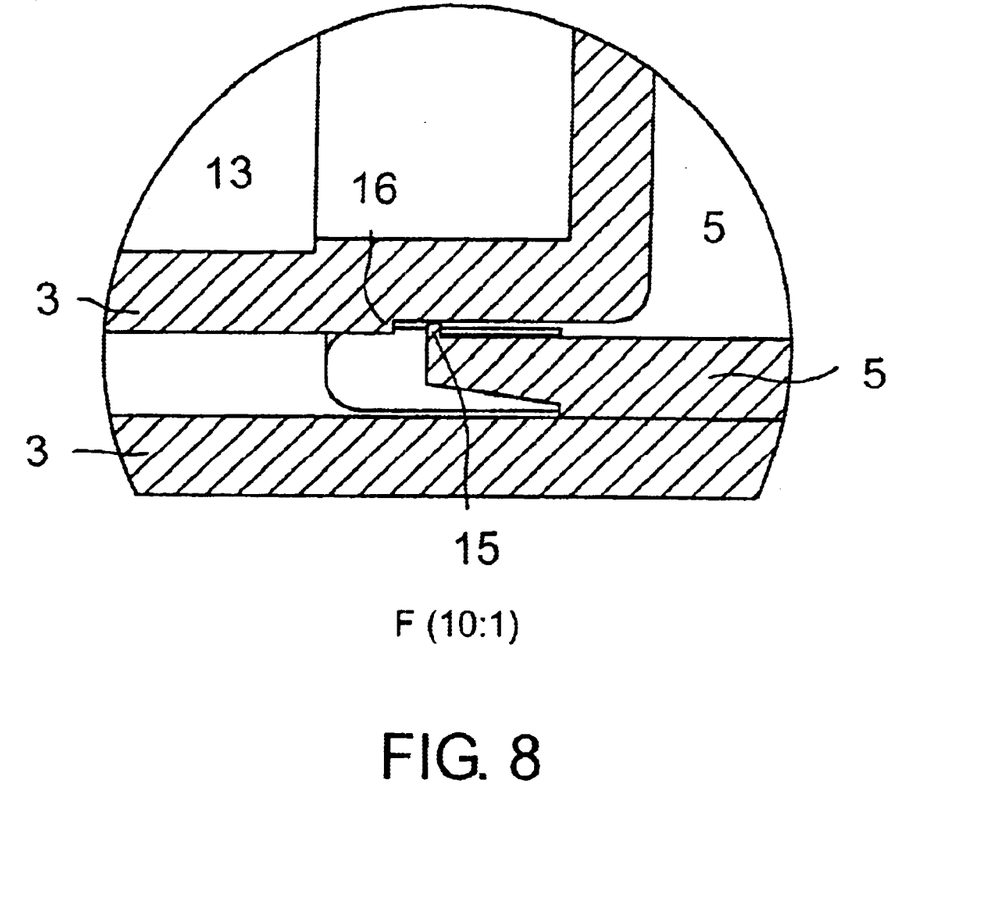
FIG. 8 shows an enlargement of a section F of FIG. 7.

FIG. 8 shows an enlargement of a section F marked on FIG. 7. This shows a mechanism according to claim 7 which help guiding the movable member from one position to another.

From the discharge tube 4 is in the upward closed position and until the discharge tube 4 rotates to the downward closed position of FIG. 5 the small projection or tenon 15 on the bowl part of the movable member can not pass the round going elevation 16 on the bowlshaped part of the base member. Only when reaching the downward closed position where the discharge tube 4 touch the lower edge 11, the small projection or tenon 15 meets a track in the elevation 16 which make it possible to push the movable member axially to the downward open position of FIG. 6. The upward side of the small projection 15 has been bevelled which make it possible to force the small projection 15 sidewards out of the track and return the discharge tube 4 to the upward closed position.

What is claimed is:

1. A valve system for a collection bag comprising:
    a base member which is secured to the collection bag; and
    a movable member which is sealingly fitted to the base member;
    the base member having an open conduit leading into the collection bag for conducting liquid to the movable member;
    the movable member having a discharge tube which is rotatably and axially displaceable along an axis of rotation with respect to the base member and which is rotated out of a plane defined by an outer surface of the collection bag;
    the movable member having at least one open position and at least one secured closed position where the discharge tube is pointing upwards;
    said discharge tube reaching an open position from said secured closed position when rotated to a position more than 90° and less than 180° from upright vertical and then axially displaced relative to said base member along the axis of rotation.

2. The valve system according to claim 1 wherein the discharge tube reaches the open position when rotated more than 100° and less than 170° from upright vertical.

3. The valve system according to claim 1 wherein the discharge tube rotates in a plane approximately perpendicular to the plane defined by the outer surface of the collection bag.

4. The valve system according to claim 1 wherein the base member has a guiding means enabling the discharge tube to return to the closed position from the open position in one movement during which the tube simultaneously rotates and moves axially.

5. The valve system according to claim 4 wherein the valve system has further guiding means positioned on surfaces of the base member and the movable member where said surfaces make contact with each other, which guiding means includes corresponding grooves and projections which assure a direction of movements made by the movable part.

6. The valve system according to claim 1 wherein the base member comprises a container which has a rotary symmetrical cavity in which a rotary symmetrical internal part of the movable member is placed, and a part of a wall of the rotary symmetrical cavity of the container is missing in order to create an opening with edges, which edges at least partly provide a guide and boundaries for movements of the discharge tube.

7. The valve system according to claim 1, wherein the discharge tube is rotated approximately 135° from upright vertical preparatory to axial displacement to reach said open position.

8. A device for collecting liquid material including a collection bag and a valve system, said valve system comprising:

a base member which is secured to the collection bag; and a movable member which is sealingly fitted to the base member;

said base member having an open conduit leading into the collection bag for conducting liquid to the movable member;

said movable member having a discharge tube which is rotatably and axially displaceable along an axis of rotation with respect to the base member and which is rotated out of a plane defined by an outer surface of the collection bag;

said movable member further having at least one open position and at least one secured closed position where the discharge tube is pointing upwards;

said discharge tube reaching the open position from the closed position when rotated between 90° and 180° from upright vertical and then axially displaced relative to said base member along the axis of rotation.

9. The device according to claim 8 wherein the discharge tube is rotated more than 100° and less than 170° from upright vertical to get to the open position.

10. The device according to claim 8 wherein the discharge tube rotates in a plane approximately perpendicular to the plane defined by the outer surface of the collection bag.

11. The device according to claim 8 wherein the collection bag is a contoured collection bag and the discharge tube in the closed position fits into a depression in a surface of the bag.

12. The device according to claim 8, wherein the discharge tube is rotated approximately 135° from upright vertical preparatory to axial displacement to reach said open position.

13. The device according to claim 8 wherein the base member has a guiding means enabling the discharge tube to return to the closed position from the open position in one movement during which the tube at the same time rotates and moves axially.

14. A valve system for a collection bag comprising:

a base member which is secured to the collection bag, said base member having tubular portion defining a substantially cylindrical cavity; and a movable member having an internal part and an external discharge tube substantially perpendicular thereto which is rotatably and axially displaceable along an axis of rotation, said internal part being at least partly hollow and having at least a portion sealingly inserted within said cavity of said tubular portion;

said base member having an open conduit leading into the collection bag for conducting liquid from said bag to the movable member;

said movable member having at least one open position in which liquid from said bag flows therethrough and at least one secured closed position where said liquid is retained within said bag; and said movable member reaching said open position when said discharge tube is rotated between 90° and 180° from the secured closed position and then axially displaced to slide said internal part further into said cavity of said base member along the axis of rotation.

15. The valve system according to claim 14, said internal part having a hole therein, said axial displacement serving to align said hole with said open conduit of said base member to allow fluid flow therethrough.

16. The valve system according to claim 14, wherein said discharge tube is rotated approximately 135° preparatory to axial displacement thereof to reach said open position.

17. The valve system according to claim 14 wherein the base member has a guiding means enabling the discharge tube to return to the closed position from the open position in one movement during which the tube simultaneously rotates and moves axially.

18. The valve system according to claim 14 wherein a part of a wall of said tubular part is missing in order to create an opening with curved edges, said edges at least partly providing a guide and boundaries for movement of the internal part of said movable member.

\* \* \* \* \*